United States Patent [19]

Lodge et al.

[11] 4,403,610
[45] Sep. 13, 1983

[54] GUN TO IMPLANT PELLETS IN ANIMALS

[75] Inventors: Robert H. Lodge, Wheeler Heights; Ian R. Phillips, Killara; Mervyn F. Reynolds, Balgowlah, all of Australia

[73] Assignee: N.J. Phillips Pty. Limited, New South Wales, Australia

[21] Appl. No.: 273,551

[22] Filed: Jun. 15, 1981

[30] Foreign Application Priority Data

Jun. 19, 1980 [AU] Australia .............................. PE4105

[51] Int. Cl.³ .............................................. A61M 5/18
[52] U.S. Cl. ..................................................... 604/61
[58] Field of Search ................................ 128/217, 215

[56] References Cited

U.S. PATENT DOCUMENTS 3,520,299  7/1970  Lott et al. ............................ 128/217
3,669,104  6/1972  Wyatt et al. ........................ 128/217
4,077,406  3/1978  Sandhage et al. .................. 128/217

Primary Examiner—John D. Yasko
Attorney, Agent, or Firm—Ladas & Parry

[57] ABSTRACT

A gun adapted to eject pellets into animals and a magazine to contain the pellets, the gun includes an ejector rod which enters the magazine to eject a pellet therefrom, and an indexing rod which engages the magazine to cause indexing thereof.

5 Claims, 7 Drawing Figures

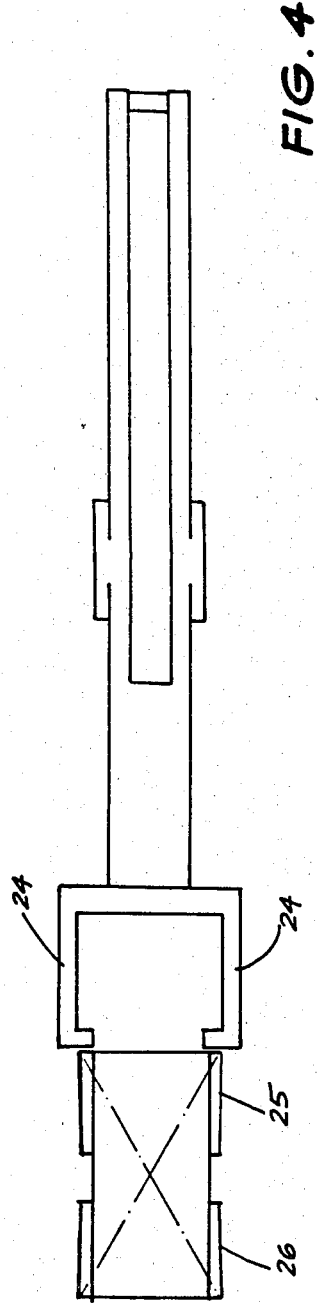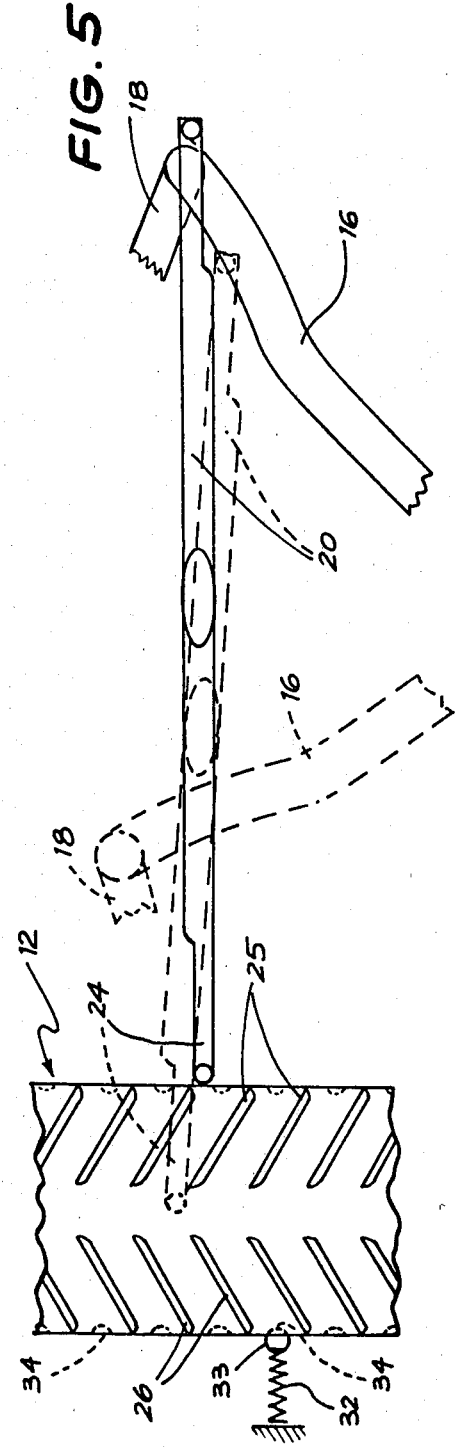

GUN TO IMPLANT PELLETS IN ANIMALS

The present invention relates to devices for the application of drugs to animals and more particularly but not exclusively to devices to implant a pellet in an animal.

It is a disadvantage of current guns which dispense drugs in the form of pellets to animals, that the guns cannot be generally reliably operated and do not employ the magazine structure to support the pellets.

It is an object of the present invention to overcome or substantially ameliorate the above disadvantages.

There is disclosed herein a gun adapted to dispense pellets from a magazine being formed with a plurality of passages within which the pellets are located, said gun comprising: a body, a trigger movably supported by the body so as to be movable by an operator from a rest position to an actuated position, a first lever coupled adjacent one of its ends to said trigger, said lever being pivotally mounted intermediate its ends, an ejector rod adapted to be moved between a first and a second position, said ejector rod being coupled to the other end of said first lever so that upon said trigger being moved to said actuated position, said lever is caused to move from said first to said second position, guide means slidably engaging said ejector rod to cause it to move along a predetermined generally linear path, magazine support means adapted to receive said magazine so that a passage thereof is located at a predetermined position located on said path, and wherein said ejector rod, when moved from said first to said second position, is caused to move through a one of said passages located at said predetermined position so as to eject a pellet located therein from within the gun.

A preferred form of the present invention will now be described by way of example with reference to the accompanying drawings, wherein:

FIG. 4 is a plan view of an indexing arm employed in the device of FIG. 1;

Figure 1:
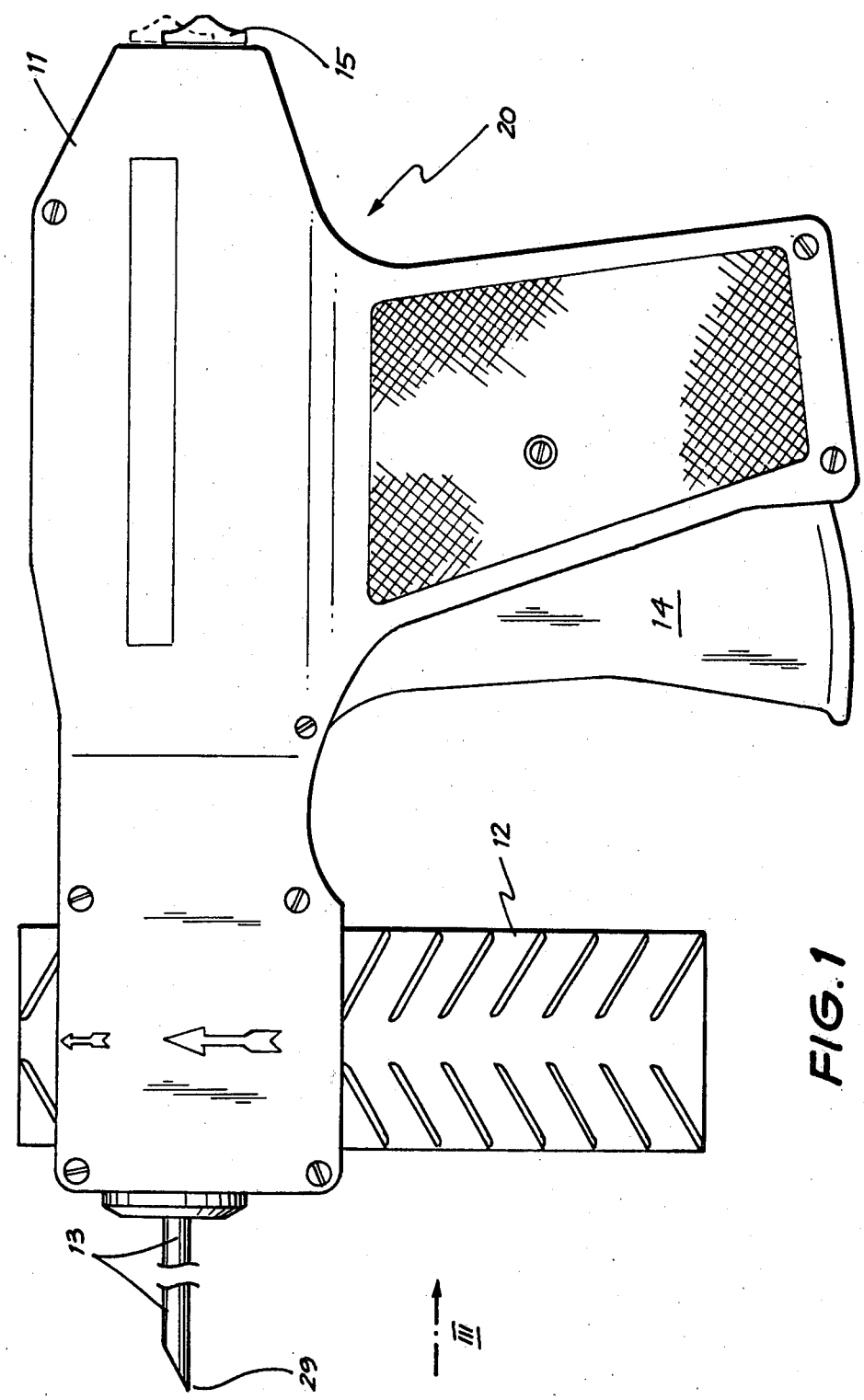
FIG. 1 is a side elevation of a device to implant pellets in an animal.
Figures 6, 7:
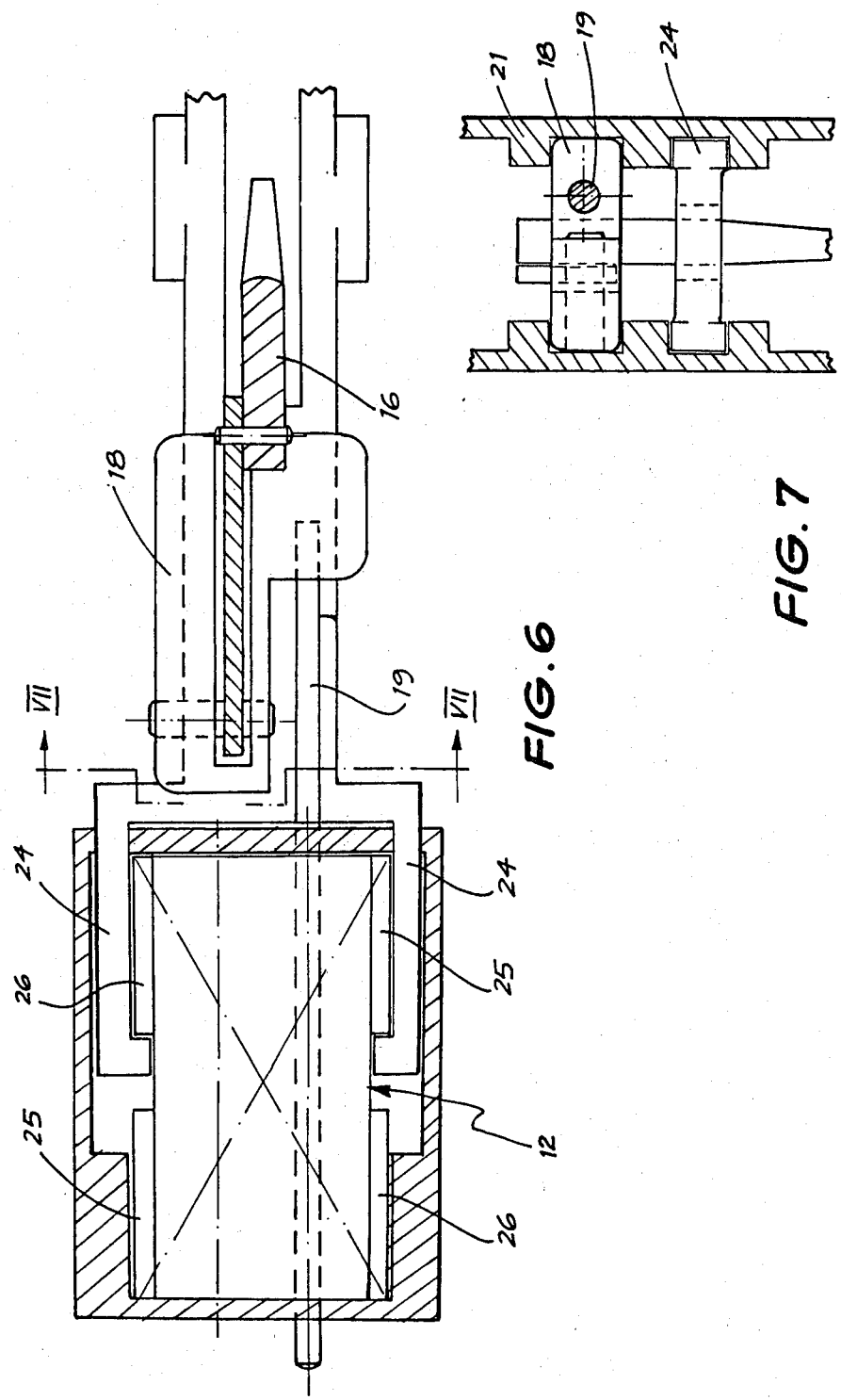

FIG. 5 schematically depicts operation of the indexing arm of FIG. 4;

FIG. 6 schematically depicts in plan view an ejection mechanism and magazine of the device of FIG. 1;

FIG. 7 is a section taken along the lines VII—VII of FIG. 6;

The device 10 of FIG. 1 includes an injection gun 11 and a magazine 12. The gun 11 is adapted to inject pellets contained in the magazine 12 through the tube 13 which is adapted to insert the pellet in an animal. The gun 11 includes a trigger 14, which, upon actuation, causes the injection of a pellet and the indexing of the magazine 12 so that the gun 11 is ready to dispense a further pellet. Additionally, there is provided a lock 15 which is movable from a lower position preventing actuation of the trigger 14 to an upper position allowing operation thereof to eject a pellet.

Figure 2:
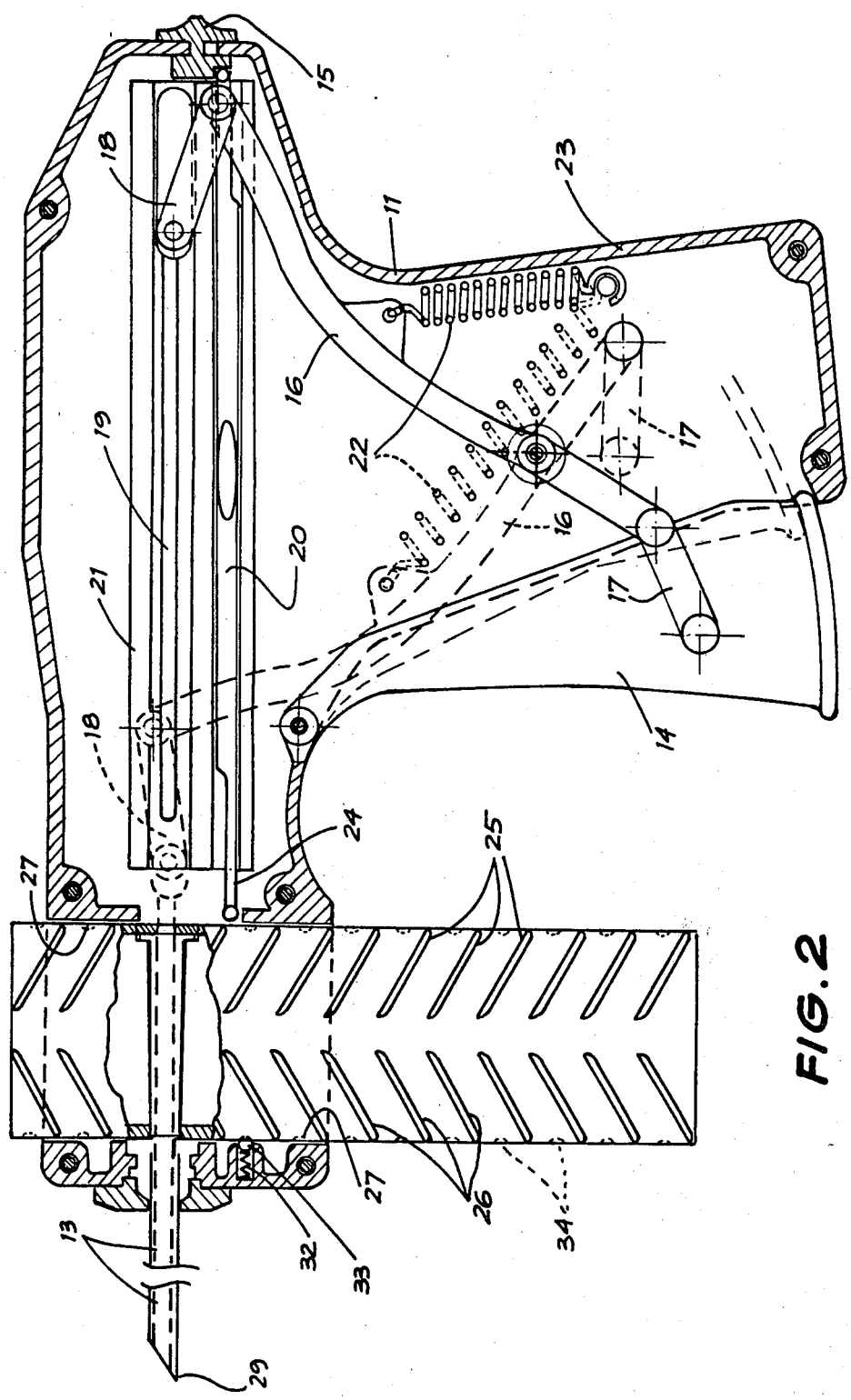
FIG. 2 is a sectioned side elevation of the device of FIG. 1.
Figure 3:
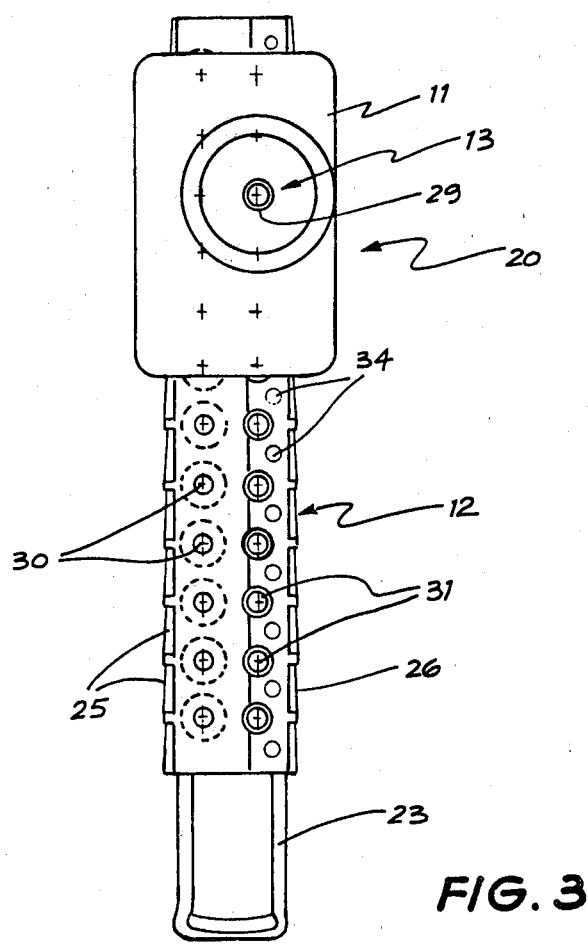
FIG. 3 is an end elevation of the device of FIG. 1 viewed in the direction 3 indicated in FIG. 1.

Now with reference to FIG. 2, the gun 11 has a hollow body which defines a chamber within which is located a lever mechanism coupled to the trigger 14. The lever mechanism includes a primary lever 16 and a secondary lever 17 pivotally coupled thereto, the secondary lever 17 is pivotally coupled to the trigger 14. To the other end of the primary lever 16 there is pivotally coupled a further secondary lever 18. Pivotally attached to the lever 18 is an ejector rod 19 which is adapted to enter the magazine 12 to eject a pellet contained therein. Additionally, there is provided an indexing rod 20 which is engaged by the primary lever 16 so as to be moved thereby to engage the magazine 12 to cause indexing thereof. The ejector rod 19 and indexing rod 20 are contained within a guide 21. The trigger 14 and lever mechanism coupled thereto are biased to a non-operative position by means of spring 22 which extends between the primary lever 16 and the handle 23. The indexing rod 20 has a forked end consisting of two arms 24 which engage the magazine 12.

The magazine 12 in this particular embodiment is adapted to dispense 24 tablets, 12 from each side of the magazine. In operation, the magazine is first placed in a first position and the pellets dispensed therefrom, thereafter the magazine is removed from within the gun and rotated 180° about a vertical axis and again inserted in the gun thereby allowing the second set of 12 pellets to be dispensed by the gun 11. The magazine 12 has two sets of lugs 25 and 26 which are engaged by the arms 24 of the indexing rod 20. It should be particularly noted that the lugs 25 and 26 are inclined to the general axis of the indexing rod 20 so that longitudinal movement thereof will cause movement of the magazine 12 in a direction transverse of the rod 20. The gun 11 includes a passage 27 to guidably receive the magazine 12. The leading portion of the gun 11 includes the tube 13 which has a sharp and pointed end 29 which receives the pellet and implants it in the animal.

Now with particular reference to the magazine 12, it should be appreciated that the magazine 12 includes two sets of passages 30 and 31 which are adapted to receive pellets to be implanted. Each set of passages 30 or 31 is associated with a particular set of projections 25 or 26.

Now with particular reference to FIG. 5, it can be seen that the rod 20 is allowed to deflect to allow it to pass over the projections 25 to enable ejection of a pellet from within the magazine 12. Upon the trigger 14 returning to its rest position, the indexing rod 20 is restricted causing it to engage the lower surfaces of the projection 25 to cause vertical movement of the magazine 12.

The magazine 12 is held in position by a ball 32 and a spring 33 which biases the ball 32 to a position located within one of recesses 34 in the magazine 12.

What we claim is:

1. A gun adapted to dispense pellets, said gun comprising a magazine formed with a plurality of passages within which the pellets are located, a plurality of projections on said magazine arranged in a predetermined relationship with respect to said passages, a gun body, a trigger movably supported by the body so as to be movable by an operator from a rest position to an actuated position, a first lever coupled adjacent one of its ends to said trigger, said lever being pivotally mounted intermediate its ends, an ejector rod adapted to be moved between a first and a second position, said ejector rod being coupled to the other end of said first lever so that upon said trigger being moved to said actuated position, said lever is caused to move from said first to said second position, guide means slidably engaging said ejector rod to cause it to move along a predetermined generally linear path, magazine support means adapted to receive said magazine so that a passage thereof is located at a predetermined position located on said path, said ejector rod, when moved from said first to said second position, being caused to move through one of said passages located at said predetermined position so as to eject a pellet located therein from within the gun, an indexing rod coupled to said other end of said lever, guide means slidably engaging said indexing rod so as to restrict the indexing rod to move along a generally linear further path between a retracted position when said trigger is in said rest position and an extended position when said trigger is in said actuated position, said further path being positioned so as to intersect projections so that upon engagement of said indexing rod with said projections said magazine is caused to move to locate a different one of said passages at said predetermined position, and wherein said indexing rod causes movement of said magazine upon movement of said indexing rod from said extended position to said retracted position.

2. The gun of claim 1 wherein said predetermined path and further path are parallel.

3. The gun of claim 2 further including spring means biasing said trigger to said rest position.

4. The gun of claim 1, 2, or 3 including a further lever attached to said other end of said first lever and said ejector rod so as to pivotally couple said first lever to said ejector rod.

5. The gun of claim 1, 2, or 3 wherein said indexing rod is resiliently deformable so as to be deflected by said projections when moving from said retracted position to said extended position.

* * * * *